United States Patent [19]

Chang et al.

[11] 4,058,576
[45] Nov. 15, 1977

[54] CONVERSION OF METHANOL TO GASOLINE COMPONENTS

[75] Inventors: Clarence D. Chang, Princeton; Shamsher S. Grover, Pennington, both of N.J.

[73] Assignee: Mobil Oil Corporation, New York, N.Y.

[21] Appl. No.: 720,870

[22] Filed: Sept. 7, 1976

Related U.S. Application Data

[63] Continuation of Ser. No. 496,434, Aug. 9, 1974, abandoned.

[51] Int. Cl.$^2$ .................. C10G 37/06; B01J 29/28
[52] U.S. Cl. .................. 260/673; 23/288 S; 208/135; 260/614 R; 260/668 R; 260/682; 260/673.5
[58] Field of Search ............ 260/673, 682, 668 R

[56] References Cited

U.S. PATENT DOCUMENTS

| | | | |
|---|---|---|---|
| 2,456,584 | 12/1948 | Gorin et al. | 260/668 R |
| 2,512,586 | 6/1950 | Stengel | 23/288 K |
| 2,992,283 | 7/1961 | Eng | 260/673 |
| 3,010,807 | 11/1961 | Christensen et al. | 23/288 |
| 3,036,134 | 5/1962 | Mattox | 260/614 |
| 3,383,428 | 5/1968 | Jones | 260/666 R |
| 3,529,033 | 9/1970 | Frilette et al. | 260/682 |
| 3,728,408 | 5/1969 | Tobias | 260/668 C |
| 3,775,501 | 11/1973 | Kaeding et al. | 260/673 |
| 3,894,107 | 7/1975 | Butter et al. | 260/668 R |

*Primary Examiner*—Delbert E. Gantz
*Assistant Examiner*—G. E. Schmitkons
*Attorney, Agent, or Firm*—Charles A. Huggett; Carl D. Farnsworth

[57] ABSTRACT

A method and sequence of process steps is described for effecting the conversion of lower alcohols comprising methanol, ethanol and propanol to gasoline boiling range component arranged to significantly extract reaction heat and selectively control the restricting of the alcohol feed through the production of ethers and olefins prior to isomerizing and aromatizing the formed olefins. A tubular reactor section is particularly relied upon for the highly exothermic olefin forming step of the combination operation.

8 Claims, 2 Drawing Figures

CONVERSION OF METHANOL TO GASOLINE COMPONENTS

This application is a Continuation of application Ser. No. 496,434, filed Aug. 9, 1974, now abandoned.

BACKGROUND OF THE INVENTION

Description of the Prior Art

U.S. Pat. No. 3,036,134 to Mattox discloses the conversion of methanol to a reaction product containing water and dimethyl ether in the presence of, as a catalyst, a crystalline aluminosilicate.

Copending application Ser. No. 387,223, filed Aug. 9, 1973, (now U.S. Pat. 3,894,107) discloses the conversion of alcohols and other similarly substituted simple hydrocarbon compounds to a reaction product containing water and highly aromatic, gasoline boilingrange hydrocarbons, by contacting such reactant with a crystalline aluminosilicate having a silica to alumina ratio of at least about 12 and a constraint index, as there defined, of about 1 to 12.

Copending application Ser. No. 387,222, filed Aug. 9, 1973 (now U.S. Pat. 3,894,106), discloses the conversion of ethers to a reaction product containing water and gasoline hydrocarbons by contacting such with a similarly defined catalyst.

The applicable class of catalysts is exemplified by ZSM-5, ZSM-11, ZSM-12, ZSM-21, and TEA Mordenite.

U.S. Pat. No. 3,702,886 issued Nov. 14, 1972 to Argauer et al. discloses ZSM-5 zeolite catalyst.

U.S. Pat. No. 3,709,979 issued Jan. 9, 1973 to Chu discloses ZSM-11 zeolite catalyst.

West German Auslegeschrift No. 2,213,109 discloses ZSM-12 catalyst.

Copending application Ser. No. 358,192, filed May 7, 1973 (now abandoned), discloses ZSM-21 catalyst.

Copending application Ser. No. 130,442, filed Apr. 1, 1971 (now abandoned), discloses TEA mordenite.

Although the above-described conversions perform exceptionally well and are unusually effective at converting various non-gasoline organic chemicals to high quality gasoline, it has been found that these conversions are exothermic to varying degrees depending on the particular reactant. For example, the amount of heat generated in the conversion of the lower alcohols to hydrocarbon product may be estimated to be in the ranges shown:

| Alcohol Reactant | Heat Produced, BTU per lb. of Hydrocarbon Product |
|---|---|
| Methanol | 1300–2000 |
| Ethanol | 280–620 |
| Propanol | 20–360 |

While it is desirable that a reaction be exothermic, since this obviates the need for an external source of heat to drive the reaction, large heat generation loads can require substantial investment in complex reactors with extensive internal cooling means, thereby detracting from the overall economic efficiency of the process. It can be seen from the above table that the conversion of methanol, and to a lesser degree of ethanol, could be considered excessively exothermic in this regard. Furthermore, because of the inherent character and efficiency of the above described crystalline aluminosilicate zeolite catalysts, the reaction of methanol, and to a lesser degree of ethanol, tend to be self-accelerating, thereby creating excessively hot local regions, where the reaction tends to go to completion, in the catalyst bed. Thus, the simple expedient of conducting the reaction partially in a first catalyst bed and completing it in a second catalyst bed is not available to facilitate heat removal. Additionally, it is generally good engineering practice to conduct reactant conversions at elevated pressures to more effectively utilize the reactor volume and process recovery of the reactor effluent. With a methanol charge, however, elevated pressures tend to produce increased quantities of 1, 2, 4, 5 tetramethylbenzene (durene). This product is believed to result at least in part from the mixing and reaction of yet-unconverted methanol with aromatic hydrocarbon products. In some situation, for example, when it is desired to utilize the conversion products as gasoline or to manufacture benzene, toluene and xylenes, durene is an undesirable by-product.

SUMMARY OF THE INVENTION

The present invention is directed to a method of using multiple stages of catalyst compositions arranged for the controlled segmented conversion or restructuring of methanol to olefins and/or gasoline boiling components. More particularly, the present invention is directed to an arrangement and sequence of processing steps for more efficiently controlling exothermic heat generated during the catalytic restructuring of lower alcohols such as methanol to olefins or gasoline boiling components. The selective reaction stages proceed through methanol conversion to dimethyl ether, conversion of ethers to olefins and conversion of olefins to gasoline boiling components. In a more particular aspect the present invention is concerned with the exothermic temperature environment and catalyst restrictions required to more selectively control exothermic heat producing reactions encountered during conversion of dimethyl ether to olefin and gasoline boiling components. In one embodiment the present invention is particularly suitable for using a ZSM-5 crystalline zeolite for the conversion of ether products of the lower alcohols to gasoline boiling components comprising aromatics and isoparaffins.

DETAILED DESCRIPTION OF INVENTION

Figure 1:
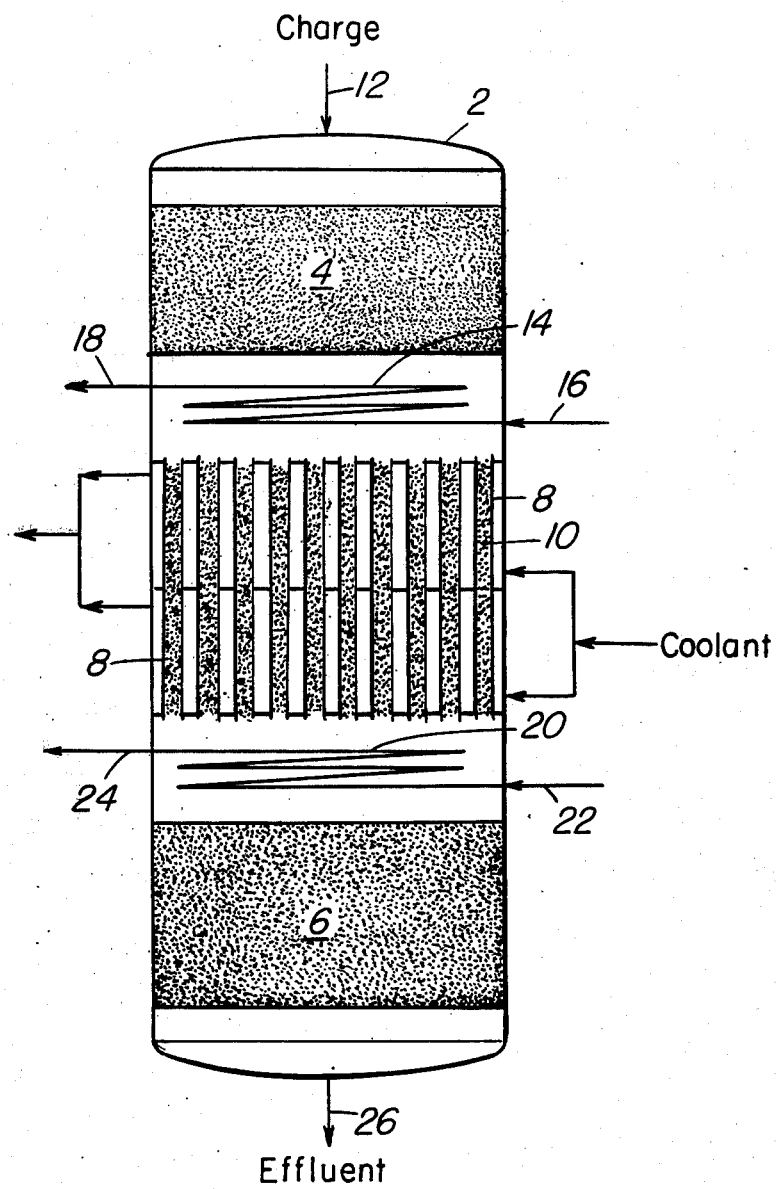

The lower alcohols that may be charged to the process of this invention, or more specifically to the first stage of the combination operation, include methanol, ethanol, propanol, and isopropanol. The feed may consist of a relatively pure single alcohol, or mixtures of these alcohols with other components such as higher alcohols. In general, any mixture comprising: methanol; or ethanol; or propanol; or isopropanol; and which is convertible with high exothermicity, is a suitable feed for the first stage of the present invention. Conversions which produce more than about 100 BTU/lb of total hydrocarbon product, and preferably more than about 200 BTU/lb of hydrocarbon product, at conversion temperature, are considered highly exothermic for the purpose of the present invention.

The preferred charges to the first stage of the present invention are ethanol and methanol. Particularly preferred are charges comprising substantial fractions, i.e. more than 25 weight percent, of methanol. Mixtures of methanol and dimethyl ether are included as preferred charges.

In the first stage of the present invention the alcohol reactant is contacted with a condensation catalyst to produce water and a predominantly aliphatic organic intermediate product. The condensation catalyst may be any catalyst which results in the intermolecular dehydration of the alcohol reactant to form an aliphatic product of higher carbon to oxygen ratio than the feed.

The condensation reactions contemplated include those that form simple and mixed ethers such as: dimethyl ether, diethyl ether, di-n-propyl ether, diisopropyl ether, methyl ethyl ether, methyl n-propyl ether, methyl isopropyl ether, ethyl n-propyl ether, ethyl isopropyl ether, and n-propyl isopropyl ether. All of these intermediates may be formed by the intermolecular dehydration of corresponding alcohol reactants, and all of these condensations are exothermic and generate heat. While this condensation reaction by itself, is generally known with alumina compositions, such as gamma alumina, it is noted that other acidic catalysts known in the art are very effective for the conversion. Such catalysts include, by way of example, liquid acids such as sulfuric and phosphoric acids, and solid inorganic and organic acidic catalysts such as phosphoric acid supported on kieselguhr, high surface area silica-alumina, acidic aluminas, acid treated clays, bauxites, and polystyrene sulfonic acids of the ion-exchange type including the macroreticular variety. For the purpose of this invention, it is preferred to use solid acidic catalysts.

Intramolecular dehydration reactions, such as the dehydration of ethanol to ethylene and water, and of propanol or isopropanol to propylene and water, although they form water and an aliphatic intermediate that has a higher carbon to oxygen ratio than the feed, these dehydration reactions are endothermic rather than exothermic.

Those skilled in the art will recognize that with methanol feed, no intramolecular dehydration is possible, and that therefore the condensation reaction can only proceed exothermically to form, for example, dimethyl ether. With ethanol, propanol, and isopropanol, on the other hand, the desired exothermic condensation and the undesired endothermic dehydration may occur over the same catalyst to different degrees under different conditions. For example, ethanol vapor passed over a certain solid acidic catalyst at about 212° F. will form, exothermically, diethyl ether; however, at substantially higher temperatures, ethanol will intramolecularly dehydrate to ethylene, which by itself is an undesirable reaction for the purpose of this invention. In fact, over certain acidic catalysts, it is well known that a dehydrogenation reaction may set in at high temperature which not only does not split out water but is also endothermic.

In one embodiment, the combination operation of the present invention comprises sequential stages of catalytic contact in which combination the first stage is a catalyst restricted exothermic heat generating operation and the second catalyst stage is exothermically one combination of the operation herein described. The first stage operation is performed in the presence of a catalytic restructuring or conversion operation which is catalytically exothermic heat generating limited by restricting the conversion of methanol to approximately an equilibrium mixture comprising dimethyl ether, methanol and water. During this first stage limited conversion operation performed with a mass of catalyst suitable for the purpose such as gamma alumina, the reactant material conversion product or first stage reaction effluent mixture is temperature raised by the catalytically generated exothermic heat to about 600° F. or 650° F. The first stage reaction effluent mixture thus formed is adjusted to a temperature within the range of 600° F. to about 800° F. by passing through an indirect heat exchange zone in indirect heat exchange with a circulating heat exchange fluid. For example, the heat exchange fluid may be water or the methanol reactant passed to the first catalyst conversion stage.

The second stage catalytic conversion operation of this invention is particularly restricted to converting the first stage effluent mixture comprising methanol, dimethyl ether and water to an olefin rich product material and/or a product rich in gasoline boiling components. The operation is highly exothermic and occurs rapidly in the presence of selected crystalline zeolites and particularly a catalyst comprising a ZSM-5 type crystalline zeolite.

In accordance with this invention, the restriction of the conversion operation comprising the second stage within limits desired, that is, the further conversion of the first stage effluent mixture is accomplished in catalyst containing reaction tubes of desired length and diameter to provide a contact time with catalyst sufficient to accomplish the reaction desired. There are a plurality of adjacent catalyst containing tubes of restricted cross-section and limited to provide a desired heat transfer relationship between catalyst particles in the reaction tubes with a temperature controlling liquid medium circulated external to the reaction tube. Thus, the second stage catalytic conversion operation is performed in a plurality of adjacent parallel arranged reaction tubes of restricted length and cross section, each of which is in indirect heat exchange with a heat exchange fluid and sized to provide the reactant contact time and temperature restrictions as herein provided. In yet another arrangement, it is contemplated passing the heat exchange fluid through the tubes and providing the catalyst in the space between tubes and/or on the surface of the tubes. In this arrangement, the reactant material may pass downwardly, upwardly or in a radial pattern through the region of catalyst contact.

In a specific embodiment, it is contemplated providing catalyst containing reaction tubes of one and one-half inch or less inside diameter and sufficiently long to accomplish the reactions desired. For example, the tubes may be 0.5 to 0.8 inch I.D. or more and from 2 to 10 feet long. The reactor tube design selected must be satisfactory for accomplishing the exothermic heat transfer requirements expected under the reaction conversion conditions desired and occurring at reactant space velocities in the range of about 5 to 50 LHSV. During traverse of the reaction tubes the first stage effluent mixture is converted with a selectivity and activity modified crystalline zeolite to produce at least an olefin rich product. The olefin rich product comprising $C_3$ and higher boiling olefins may be recovered as such or further converted as herein provided. The olefin rich product formed is maintained at a temperature in the range of 600° F. to about 850° F. during contact with the second stage catalyst reaction tube. Water or any other suitable heat exchange fluid material may be used in indirect heat exchange relationship with the catalyst and reactants in the reaction tubes to remove generated heat as desired.

The olefin rich product comprising $C_3$ and higher boiling olefins formed in the reaction tubes or external thereto may be allowed to react further in the zone of reaction tubes to form gasoline boiling range components or be recovered as an olefin rich product of the process. On the other hand, the zone of reaction tubes may be restricted to accomplish the formation of olefins which olefins are recovered therefrom and temperature adjusted before passing in contact with a third catalyst stage arranged and maintained under conditions to accomplish a conversion of the olefin rich product to gasoline boiling range product. Thus, it is contemplated providing three stages of catalyst contact in a single reaction zone wherein the second and third reaction stage comprises said catalyst containing reaction tubes or the third stage of reaction may be retained in a separate catalyst reaction vessel so that flexibility may be provided for recovering an olefin rich product from the tubular reactor stage before encountering the third stage of catalyst. On the other hand, as mentioned above it is contemplated varying the product recovered from the tubular reaction stage between an olefin rich product or gasoline boiling range product. Thus the tubular reaction stage will be used for forming primarily olefins from the ether feed of the first stage or it may be used to further convert the formed olefins in a downstream portion of the tube to gasoline boiling components. It is contemplated varying the product obtained from the tubular reaction section between an olefin rich product and/or a gasoline boiling range component product by varying the reactant space velocity and thus its contact time within the catalyst containing reaction tube. Gasoline boiling range products are formed preferably at the longer reactant residence times.

The $C_3$ olefin rich product recovered from the tubular second stage catalytic conversion operation may be temperature adjusted before further conversion in a separate third stage by indirect heat exchange means to a temperature within the range of 600° F. to about 850° F. Thereafter the temperature adjusted $C_3$ olefin rich stream is passed in contact with a ZSM-5 type crystalline zeolite catalyst of desired selectivity and activity maintained at a temperature within the range of 600° F. to about 850° F. and a residence time within the range of 5 to about 15 seconds. The reaction conditions selected are those particularly promoting the conversion of the olefins to aromatics and isoparaffins boiling in the gasoline boiling range.

In the combination operations above identified, the processing restriction relied upon for converting methanol to olefin and/or gasoline boiling constituents significantly improves the product yield-octane relationship based on feed by restricting undesired side product reactions.

The class of zeolites utilized in the process of this invention other than the first catalyst stage has some unusual properties. These zeolites by themselves can transform aliphatic hydrocarbons to aromatic hydrocarbons in commercially desirable yields. Although they have unusually low alumina contents, i.e., high silica to alumina ratios, they are very active even when the silica to alumina ratio exceeds 30. In fact product advantages during the formation of aromatics has been found by limiting the silica to alumina ratio below 60 thereby reducing the formation of durene and permitting the use of higher pressures. The activity and selectivity characteristics of these crystalline zeolites are somewhat surprising since the alumina in the zeolite framework is believed responsible for catalytic activity. They retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity.

An important characteristic of the crystal structure of the class of zeolites particularly suitable for use herein is that the zeolite provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention, possess, in combination: a silica to alumina ratio of at least about 12; with some improved results obtained when using a silica to alumina ratio in the range of 30 to 70 to reduce the formation of durene and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these zeolites ineffective. Twelve-membered rings do not generally appear to offer sufficient constraint to produce the advantageous conversions, although structures can be conceived, due to pore blockage or other cause, that may be operative.

FIG. 1 schematically provides one arrangement of apparatus for housing a plurality of separate sequentially arranged catalyst conversion zones for effecting the conversion of methanol to gasoline boiling components.

Figure 2:
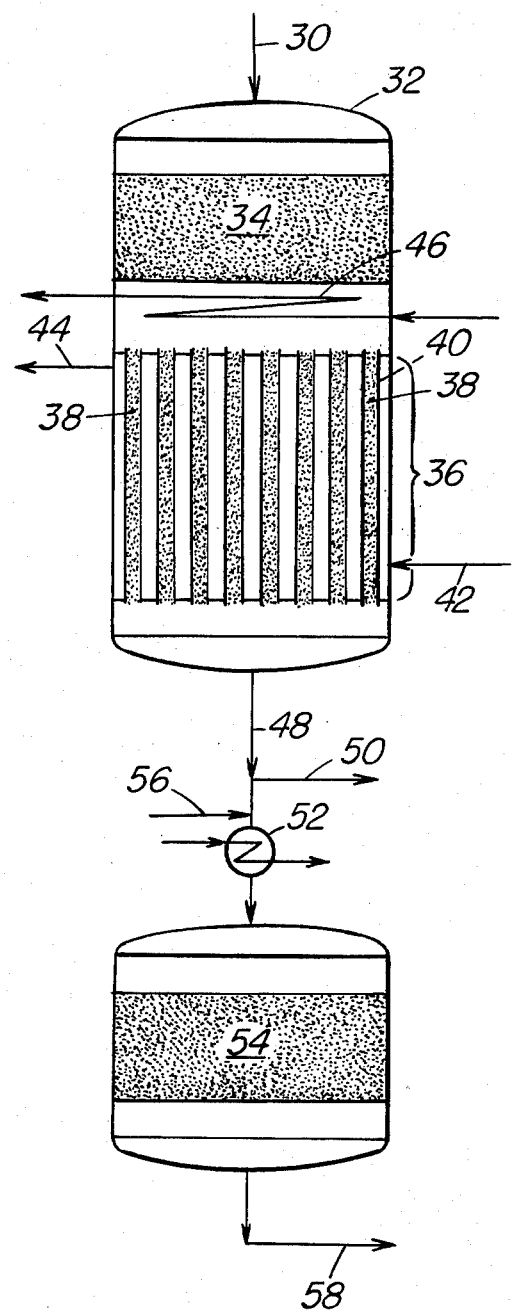

FIG. 2 is a schematic modification of FIG. 1 arrangement of apparatus comprising a plurality of separate sequentially arranged catalyst conversion zones for effecting the conversion of methanol to either an olefin rich product stream and/or a gasoline boiling component stream.

Referring now to FIG. 1 by way of example there is shown an elongated upright vessel 2 comprising an upper fixed bed of catalyst 4, a bottom fixed bed of catalyst 6 and an intermediate reaction section comprising a plurality of parallel arranged reaction tubes 8 containing catalytic material 10. The reaction tubes are in indirect heat exchange relationship with a heat exchange fluid such as boiler feed water (BFW) or other suitable heat exchange fluid. The catalyst comprising bed 4 is any suitable solid catalyst material which may be relied upon to convert methanol to particularly dimethyl ether or a product stream rich in other product such as an equilibrium product stream. One catalyst suitable for this purpose is gamma alumina. Catalyst material 6 in the bottom catalyst bed and 10 in the tubular reactor is preferably a crystalline zeolite of the ZSM-5 type and particularly one suitable for converting within the reaction tubes, and approximate equilibrium product of first catalyst stage reaction effluent separated from bed 4 into at least an olefin rich product stream. The olefin product stream is then passed in this specific arrangement in contact with the crystalline zeolite catalyst comprising bed 6 under conditions suitable for converting the olefin rich stream to gasoline boiling components.

In the arrangements of FIG. 1, a methanol rich feed stream such as crude methanol comprising from 10 to 16 weight percent water in a vapor, liquid or mixed phase condition is introduced to reactor 2 by conduit 12 at a temperature selected from within the range of 600° to 800° F. The introduced methanol feed is then caused to pass through a fixed bed of gamma alumina catalyst particles under conditions particularly restricted to effect conversion of methanol to dimethyl ether, methanol and water in a first stage effluent approximately an equilibrium mixture. The first stage effluent mixture is then temperature adjusted to within the range of 600° F. to 750° F. by passing in indirect heat exchange relationship with heat exchange means 14 to which a suitable heat exchange fluid is introduced by conduit 16 and removed therefrom by conduit 18. It is contemplated using the methanol feed as the heat exchange fluid introduced by conduit 16. The first stage effluent mixture adjusted to a temperature of about 650° F. is then caused to pass through a plurality of parallel arranged catalyst containing heat exchange tubes of low pressure drop design, generally not exceeding about 50 psig at a velocity providing a residence time in contact with the catalyst not exceeding about 15 seconds under temperature conditions restricted to within the range of 650° to 850° F. It is important in this specific example that the highly exothermic reaction conditions of the second stage tubular catalytic conversion operation be selected and restricted to effect primarily the conversion of the first stage effluent mixture to particularly olefinic constituents. In a particular aspect it is preferred that the concentration of dimethyl ether, for example, in the second stage effluent be restricted to less than 5 weight percent.

The olefin rich product removed from the reaction tubes is then indirectly temperature adjusted by heat exchange means 20 supplied with heat exchange fluid by conduit 22. Heat exchange fluid thus used is recovered by conduit 24.

The olefin rich product thus obtained and temperature adjusted to within the range of 600° to 850° F. is then passed in contact with a mass of zeolite catalyst 6 maintained under conditions particularly selected to accomplish conversion of the olefin rich feed to gasoline boiling components. The third catalyst mass particularly comprises a ZSM-5 type crystalline zeolite. The conversion of the olefin rich material stream is accomplished in the presence of the ZSM-5 type catalyst at a temperature within the range of 700° F. to about 900° F., at a reactant residence time within the range of 5 to 15 sec. The effluent of the third stage catalytic conversion operation comprising gasoline boiling components is removed from the vessel 2 by conduit 26 and passed to product recovery equipment not shown.

The combination operation of the present invention is particularly directed to selectively controlling intermediate reactions in the reaction train in a direction which will particularly restrict the formation of $C_2$ and lower boiling saturated and unsaturated constituents in preference to the formation of $C_3$ components convertible to aromatics and isoparaffins preferentially to the formation of durene. Thus, as pointed out above, the tubular reaction section of the combination operation is maintained under conditions which will particularly provide olefinic components, comprising preferably $C_3+$ olefinic components, readily isomerized and cyclized by the ZSM-5 crystalline zeolite under selected operating conditions. The gasoline boiling range hydrocarbon components produced by the combination operation of this invention are separated from other product components of the reaction sequence by substantially any suitable means such as by flash separation and distillation.

FIG. 2 departs from FIG. 1 by separating the third stage of catalyst into a separate vessel or conversion zone and providing for the separate recovery of the product effluent of the tubular reaction section in part or total is desired. Provision is also made for adding additional materials from external sources to the effluent passed from the tubular reaction section to the third stage of catalyst. Thus the arrangement of FIG. 2 permits the recovery of olefin rich material as a product of the tubular reaction section, gasoline boiling range components comprising aromatics as product of the tubular reaction section and gasoline boiling range product from the third catalyst conversion stage.

Referring now to FIG. 2, a methanol feed is introduced by conduit 30 to vessel 32 housing an upper catalyst bed 34 and a tubular reactor section 36. Catalyst bed 34 comprises a dehydration catalyst for converting methanol to an ether rich first effluent stream and tubular reactor section 36 houses a crystalline zeolite catalyst suitable for converting the ether rich stream to a product stream rich in $C_3$ and higher olefins and/or gasoline boiling range produces depending upon the reaction conditions selected and maintained therein. The tubular reactor section contains a crystalline zeolite catalyst of the ZSM-5 type 38 discussed above and is relied upon to form primarily an olefin rich product stream or a stream rich in gasoline boiling range components comprising aromatics and isoparaffins as discussed above. A suitable heat exchange fluid is provided in the space about the reaction tubes 40 by conduit 42. The heated fluid is removed therefrom by conduit 44. Indirect heat exchange means 46 is provided for adjusting the temperature of the effluent from the first catalyst stage before it contacts catalyst in the reaction tubes as more specifically discussed with respect to FIG. 1. Reactor tubes 40 are sized in diameter and length to accommodate the conversion of the ether rich effluent to either olefin rich products or products comprising gasoline boiling range components in response to changes in temperature, space velocity and pressure. When the tubular reactor section is relied upon for the formation of aromatics and isoparaffins it has been found desirable to rely upon a crystalline zeolite comprising a silica-alumina ratio less than 60 but above about 30. The product effluent of the tubular reaction section is recovered by conduit 48 and may be withdrawn by conduit 50 if desired. On the other hand, the effluent may be passed through heat exchanger 52 and thence to a further stage of catalyst conversion 54 such as disclosed with respect to catalyst bed 6 of FIG. 1. Additional outside source material suitable for conversion by catalyst bed 54 with the product effluent of the tubular reactor section above discussed may be added by conduit 56. For example, streams rich in $C_3$ to $C_5$ olefins and olefinic naphtha material may be added by conduit 56 for upgrading in catalyst bed 54. Heat exchanger 52 is provided for adjusting the temperature of the charge passed in contact with bed 54 to within the range of about 700° F. up to about 900° F. The products of the third stage of catalyst contact are withdrawn by conduit 58 for separation into desired product.

It is clear from the above discussion that the processing concepts herein defined contemplate a three stage operation, a two stage operation and the recovery of either an olefin rich product stream, a gasoline boiling range product or a combination of both.

Having thus generally discussed the invention and described in specific embodiment in support thereof, it is to be understood that no undue restrictions are to be imposed by reason thereof except as defined by the following claims.

We claim:

1. In the process of converting at least one lower aliphatic alcohol having from 1-3 carbon atoms into hydrocarbon products comprising olefins, wherein said alcohol is contacted with a condensation catalyst at elevated temperatures in a first reaction zone in order to obtain a product comprising a mixture of water and at least one ether, and said product from said first reaction zone is therefore contacted with a crystalline aluminosilicate zeolite in a second reaction zone, said zeolite having a pore size greater than about 5 Angstrom Units, a silica to alumina ratio of at least about 12, and a constraint index of about 1 to 12 at elevated temperatures in order to obtain said hydrocarbon product comprising olefins, the improvement which comprises:
   a. adjusting the temperature of the first reaction zone product to a temperature within the range of 600° F to about 800° F;
   b. introducing said product from step (a) into said second reaction zone, wherein said crystalline aluminosilicate zeolite is confined within a plurality of adjacent elongated confined reaction zones surrounded by a heat exchange fluid; and
   c. controlling exothermic reaction conditions within said elongated confined reaction zone in order to obtain said hydrocarbon product comprising olefins.

2. The process of claim 1, wherein said $C_1$–$C_3$ aliphatic alcohol is methanol.

3. The process of claim 1, wherein said crystalline aluminosilicate zeolite present in said second reaction zone is ZSM-5.

4. The method of claim 1, wherein a hydrocarbon product comprising olefins is recovered from the elongated confined reaction zone and converted to aromatic compounds in a separate down-stream reaction zone under less severe exothermic reaction conditions than encountered in said elongated confined reaction zone said down-stream reaction zone containing a crystalline aluminosilicate zeolite having a pore size greater than about 5 Angstrom Units, a silica to alumina ratio of at least about 12 and a constraint index of about 1–12.

5. The process of claim 4, wherein said crystalline aluminosilicate zeolite is ZSM-5.

6. The method of claim 4 wherein olefin rich gases from a source other than said elongated confined reaction zones are also passed to said separate down-stream reaction zone.

7. The method of claim 1 wherein the heat release in the initial portion of the elongated confined reaction zone is greater than in a down-stream portion thereof and is therefore separately controlled by the flow of heat exchange fluid about the reaction zone.

8. The method of claim 1 wherein the concentration of the crystalline zeolite catalyst employed in the elongated confined reaction zone is maintained within limits substantially restricting the exothermic reaction heat release.

* * * * *

UNITED STATES PATENT AND TRADEMARK OFFICE
CERTIFICATE OF CORRECTION

PATENT NO. : 4,058,576
DATED : November 15, 1977
INVENTOR(S) : CLARENCE D. CHANG and SHAMSHER S. GROVER It is certified that error appears in the above-identified patent and that said Letters Patent are hereby corrected as shown below:

| | |
|---|---|
| Column 1, line 17 | "boilingrange" should be --boiling-range--. |
| Column 7, line 19 | After "olefin" add --rich--. |
| Column 7, line 24 | "arrangements" should be --arrangement--. |
| Column 9, line 29 | After described, "in" should be --a--. |
| Column 9, line 42 | "therefore" should be --thereafter-- |
| Column 10, line 36 | "beat" should be --heat--. |

Signed and Sealed this

Fourth Day of April 1978

[SEAL]

Attest:

RUTH C. MASON
Attesting Officer

LUTRELLE F. PARKER
Acting Commissioner of Patents and Trademarks